(12) United States Patent
Neumann

(10) Patent No.: US 11,984,215 B2
(45) Date of Patent: *May 14, 2024

(54) METHODS AND SYSTEMS FOR INFORMING PRODUCT DECISIONS

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

(*) Notice: Subject to any disclaimer, the term of this patent is extended or adjusted under 35 U.S.C. 154(b) by 228 days.

This patent is subject to a terminal disclaimer.

(21) Appl. No.: 17/514,303

(22) Filed: Oct. 29, 2021

(65) Prior Publication Data
US 2022/0051782 A1    Feb. 17, 2022

Related U.S. Application Data

(63) Continuation of application No. 16/729,326, filed on Dec. 28, 2019, now Pat. No. 11,222,719.

(51) Int. Cl.
*G16H 20/60* (2018.01)
*G06F 18/214* (2023.01)
(Continued)

(52) U.S. Cl.
CPC .......... *G16H 20/60* (2018.01); *G06F 18/214* (2023.01); *G06F 18/23* (2023.01);
(Continued)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

| 2011/0238585 A1* | 9/2011 | Classen .................. G16H 70/60 705/310 |
| 2016/0232311 A1* | 8/2016 | Segal ..................... G06N 20/00 |

(Continued)

OTHER PUBLICATIONS

Wang et al. 2009, "Extract interaction detection methods from the biological literature," BMC Bioinformatics. Jan. 30, 2009;10 Suppl 1(Suppl 1):S55. doi: 10.1186/1471-2105-10-S1-S55. PMID: 19208158; PMCID: PMC2648772.*

(Continued)

*Primary Examiner* — Robert W Morgan
*Assistant Examiner* — Charles P Coleman
(74) *Attorney, Agent, or Firm* — Caldwell Intellectual Property Law

(57) ABSTRACT

A system for informing product decisions, the system including a computing device configured to receive a conditional complaint relating to a user; select an article of interest intended to correct the conditional complaint; retrieve a biological extraction relating to the user; generate, a classifier, wherein the classifier comprises a machine-learning model trained by training data including a plurality of biological extractions and a plurality of correlated articles of interest, and wherein the classifier is configured to receive the user biological extraction as an input and output a tolerability score as a function of the training data; and display the tolerability score.

20 Claims, 7 Drawing Sheets

(51) Int. Cl.
*G06F 18/23* (2023.01)
*G06F 18/2415* (2023.01)
*G06F 18/2433* (2023.01)
*G06N 7/01* (2023.01)
*G06N 20/00* (2019.01)
*G06V 10/762* (2022.01)
*G06V 10/764* (2022.01)
*G16H 50/30* (2018.01)

(52) U.S. Cl.
CPC .... *G06F 18/24155* (2023.01); *G06F 18/2433* (2023.01); *G06N 7/01* (2023.01); *G06N 20/00* (2019.01); *G06V 10/762* (2022.01); *G06V 10/764* (2022.01); *G16H 50/30* (2018.01)

(58) Field of Classification Search
CPC ........ G16H 20/13; G16H 20/17; G16H 30/00; G16H 40/00; G16H 50/00; G16H 70/00; G16H 80/00; G16H 20/60; G16H 50/30; G06Q 50/22–24; G06N 20/00; G06N 7/01; G06V 10/762; G06V 10/764; G06F 18/214; G06F 18/2433; G06F 18/23; G06F 18/24155

USPC .................................................. 705/2, 3, 20
See application file for complete search history.

(56) References Cited

U.S. PATENT DOCUMENTS

2017/0310775 A1* 10/2017 Tatourian ............... H04L 67/535
2018/0240542 A1* 8/2018 Grimmer ................ A61P 25/00
2019/0295440 A1* 9/2019 Hadad .................. G06F 40/295

OTHER PUBLICATIONS

Yin et al. 2017, "A Health Decision Support System for Disease Diagnosis Based on Wearable Medical Sensors and Machine Learning Ensembles," in IEEE Transactions on Multi-Scale Computing Systems, vol. 3, No. 4, pp. 228-241, Oct. 1-Dec. 2017, doi: 10.1109/TMSCS.2017.2710194.*

* cited by examiner

METHODS AND SYSTEMS FOR INFORMING PRODUCT DECISIONS

CROSS-REFERENCE TO RELATED APPLICATIONS

This application is a continuation of Non-provisional application Ser. No. 16/729,326 filed on Dec. 28, 2019 and entitled "METHODS AND SYSTEMS FOR INFORMING PRODUCT DECISIONS," the entirety of which is incorporated herein by reference.

FIELD OF THE INVENTION

The present invention generally relates to the field of artificial intelligence. In particular, the present invention is directed to methods and systems for informing product decisions.

BACKGROUND

Accurate selection and utilization of products can be challenging. Frequently, consumers are overwhelmed by the plethora of products to choose from. This is further challenged by the lack of information and understanding as to how products will affect each person's body.

SUMMARY OF THE DISCLOSURE

In an aspect, a system for informing product decisions, the system including a computing device configured to receive a conditional complaint relating to a user; select an article of interest intended to correct the conditional complaint; retrieve a biological extraction relating to the user; generate, a classifier, wherein the classifier comprises a machine-learning model trained by training data including a plurality of biological extractions and a plurality of correlated articles of interest, and wherein the classifier is configured to receive the user biological extraction as an input and output a tolerability score as a function of the training data; and display the tolerability score.

In an aspect, a method of informing product decisions, the method including receiving by a computing device, a conditional complaint relating to a user; selecting by the computing device, an article of interest intended to correct the conditional complaint; retrieving by the computing device, a biological extraction relating to the user; generating by the computing device, a classifier, wherein the classifier comprises a machine-learning model trained by training data including a plurality of biological extractions and a plurality of correlated articles of interest, and wherein the classifier is configured to receive the user biological extraction as an input and output a tolerability score as a function of the training data; and displaying by the computing device, the tolerability score.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for informing product decisions. In an embodiment, a computing device locates an article of interest for a user. An article of interest may be located based on user geolocation data and/or user climate data in combination with machine-learning algorithms. An article of interest may also be located based on a user selection displayed to a user on a graphical user interface. A computing device generates using ingredient training data and a classification algorithm an ingredient metabolic classifier. The ingredient metabolic classifier uses a biological extraction as an input and outputs an ingredient metabolic profile. A computing device identifies an ingredient contained within an article of interest and determines the tolerability of the article of interest for the user.

Figure 1:
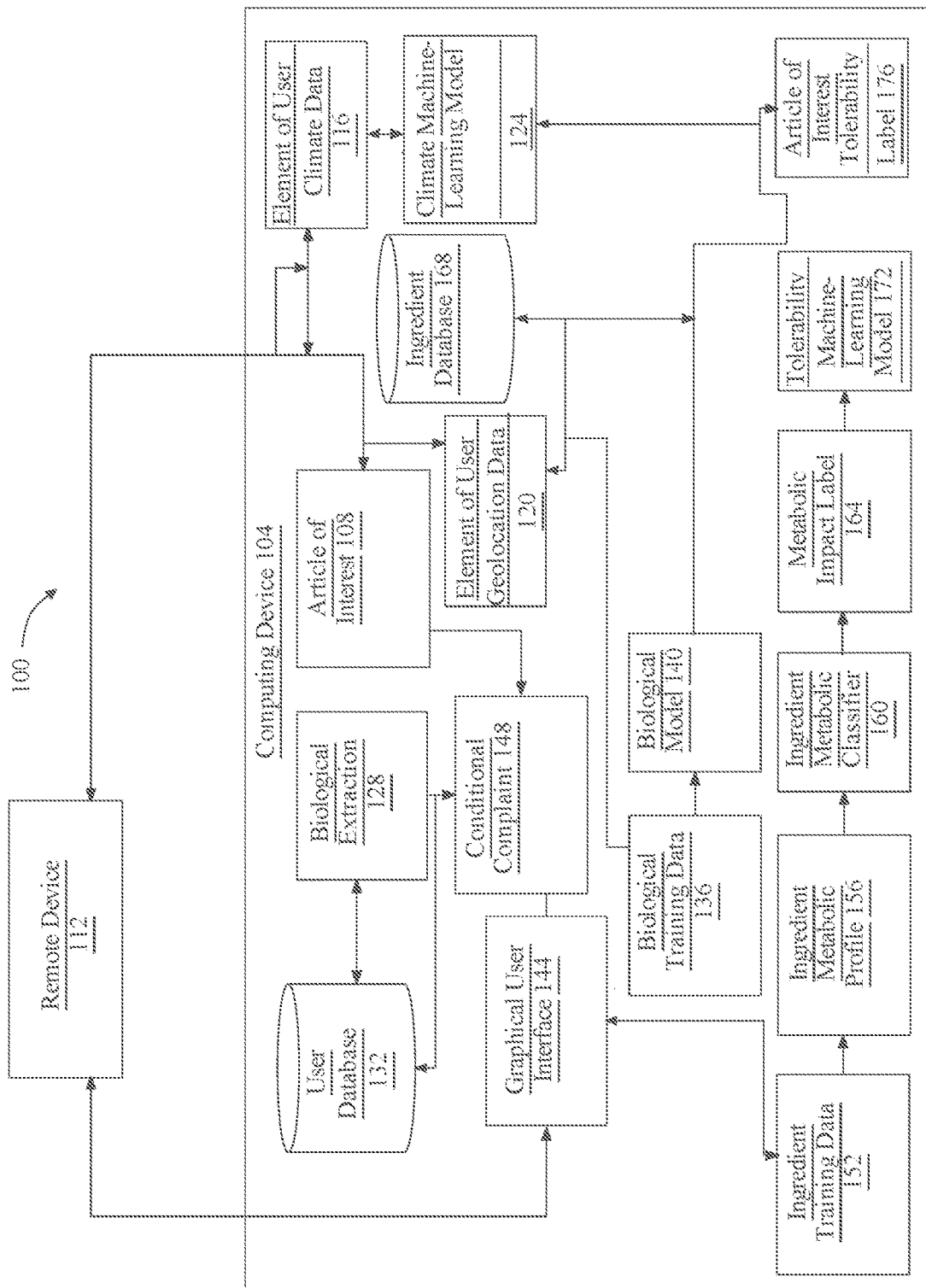
FIG. 1 is a block diagram illustrating an exemplary embodiment of a system for informing product decisions.

Referring now to FIG. 1, an exemplary embodiment of a system 100 for informing product decisions is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to locate an article of interest 108 for a user. An "article of interest," as used in this disclosure, is any product intended to enhance and/or alter the appearance, fragrance, and/or texture of a human body. A product may include any material intended for use as an ingredient of a cosmetic product. A product may be composed of one or more chemical compounds. Chemical compounds may include natural sources, synthetic sources, and/or artificial sources. Natural sources may include any chemical compound and/or substance produced by a living organism. Natural sources may include one or more handmake and/or certified organic products. Synthetic sources may include one or more products produced by chemical reactions. Artificial sources may include any humanly contrived products. An article of interest 108 may be intended to be applied externally including but not limited to skin-care creams, lipsticks, eye makeup, facial makeup, body makeup, towelettes, contact lenses, deodorants, creams, lotions, powders, perfumes, bath products, bath oils, body salts, body scrubs, body lotions, body creams, body butters, nail polish, hand sanitizer, hair color, hair spray, hair gel, shampoo, conditioner, sunscreen, lip gloss, lip liner, lip plumper, lip balm, lip stain, lip conditioner, lip primer, lip booster, lip butter, makeup primer, makeup concealer, foundation, face powder, rogue, blush, highlight, bronzer, mascara, eye shadow, eye liner, eyebrow pencils, setting spray, false eyelashes, contouring, cleaners, foaming washes, cleansing oil, toners, facial masks, exfoliants, moisturizers, tools utilized to apply products including foundation brush, concealer brush, blush brush, powder brush, highlight brush, eyeshadow brush, eyeliner brush, lip brush, and the like.

With continued reference to FIG. 1, computing device 104 may locate an article of interest 108 by receiving a user request such as from a remote device 112. A user may inquire about a particular product, such as a specific brand and shade of lipstick. A user may inquire about a class and/or category of articles of interest such as shampoos or hair gels. A user may transmit an article of interest 108 from a remote device 112 to computing device 104 utilizing any network methodology as described herein. A remote device 112 may include without limitation, a display in communication with computing device 104, where a display may include any display as described herein. Remote device 112 may include an additional computing device, such as a mobile device, laptop, desktop, computer and the like.

With continued reference to FIG. 1, computing device 104 may locate an article of interest 108 based on climate data based on where a user is currently located and/or where a user current presides. Computing device 104 receives an element of user climate data 116 transmitted from remote device 112. An "element of user climate data," as used in this disclosure, is any data describing weather conditions prevailing in an area in general where a user resides, spends time working, commutes to and from and the like. An element of user climate data 116 may describe the average temperature, humidity, atmospheric pressure, wind, and/or precipitation in a specific geographical location. For instance and without limitation, a user who resides in Hawaii may generate an element of user climate data 116 that describes moderate temperatures that range between 70 degrees Fahrenheit and 90 degrees Fahrenheit year round with moderate humidity. In yet another non-limiting example, a user who resides in Portland, Maine may generate an element of user climate data 116 that describes dry winters with temperatures that do not exceed 40 degrees Fahrenheit on average, and wet humid summers that see moderate rainy precipitation with temperatures that do not exceed 85 degrees Fahrenheit on average. In an embodiment, an element of user climate data 116 may include an element of user geolocation data 120 that may be utilized by computing device 104 to determine an element of user climate data 116. An "element of user geolocation," as used in this disclosure, is an identification of a real-world geographical location of a user. An element of user geolocation data 120 may be obtained from a radar source, remote device 112 such as a mobile phone, and/or internet connected device location. An element of user geolocation may include a global positioning system (GPS) of a user. An element of user geolocation may include geographic coordinates that may specify the latitude and longitude of a particular location where a user is located.

With continued reference to FIG. 1, computing device 104 generates a climate machine-learning model 124. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, a machine learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

With continued reference to FIG. 1, a "climate machine-learning model" as used in this disclosure, is a machine-learning model that utilizes climate data as an input and outputs articles of interest. Computing device 104 generates a climate machine-learning model 124. Generating a climate machine-learning model may include performing a series of one or more calculations, algorithms, and/or equations. For instance and without limitation, climate machine-learning model 124 may utilize climate data that indicates a user lives in the dry desert climate of Phoenix, Arizona in combination with climate machine-learning model 124 to output an article of interest 108 that includes a moisturizer. In yet another non-limiting example, climate machine-learning model 124 may utilize climate data that indicates a user works in an office building that uses steam heating eight months of the year in combination with climate machine-learning model 124 to output an article of interest 108 that includes a hydrating serum. Computing device 104 identifies an article of interest 108 as a function of generating a climate machine-learning model 124.

With continued reference to FIG. 1, computing device 104 is configured to receive a biological extraction 128. A "biological extraction" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 180 as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anaerobic bacterial cultures, fecal short chain fatty acids, beta-glucuronidase, cholesterol, chymotrypsin, fecal color, *cryptosporidium*

EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MM fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as Methanobrevibacter smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's *muciniphila, Anaerotruncus colihominis*, bacteriology, Bacteroides vulgates', Bacteroides-Prevotella, Barnesiella species, Bifidobacterium longarm, *Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocortisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, one or more user biological extractions 128 may be stored in user database 132, as described in more detail below. User database may be implemented, without limitation, as a relational database, a key-value retrieval datastore such as a NOSQL database, or any other form or structure for use as a datastore that a person skilled in the art would recognize as suitable upon review of the entirety of this disclosure.

With continued reference to FIG. 1, computing device 104 may utilize a biological extraction 128 to locate an article of interest 108. Computing device 104 may generate a clustering algorithm utilizing biological training data 136 to generate a biological model 140. A "clustering algorithm," as used in this disclosure, is any process and/or calculation that involves grouping a set of objects and/or data in a way that objects and/or data in the same group or cluster are more similar to each other than to those in other groups or clusters. Clustering algorithm may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like.

With continued reference to FIG. 1, computing device 104 may generate a clustering algorithm utilizing biological training data. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, "biological training data," as used in this disclosure, is training data that includes a plurality of biological extraction 128 and a plurality of correlated articles of interest 108. Computing device 104 utilizes a clustering algorithm and biological training data 136 to generate a biological model 140. A "biological model," as used in this disclosure is a machine-learning model that utilizes a biological extraction 128 as an input and outputs articles of interest. Generating a biological model 140 may include performing a series of one or more calculations, algorithms, and/or equations. Computing device 104 determines using biological model 140 an article of interest 108. For example, computing device 104 may utilize a user biological extraction 128 that shows the user has high urinary levels of heavy metals such as lead and mercury in combination with generating biological model 140 utilizing biological training data 136 to determine an article of interest 108 such as a shampoo that does not contain heavy metals including lead and mercury, and that also does not contain any precursors to heavy metals.

With continued reference to FIG. 1, computing device 104 may locate an article of interest 108 based on articles of interest that may be available for a user to purchase within a certain geolocation of the user. Computing device 104 may receive an element of user geolocation data 120 from a remote device 112. An element of user geolocation data 120 includes any of the elements of user geolocation data as described above. Computing device 104 identifies articles of interest available to be acquired within the user geolocation. Articles of interest within the user geolocation may include a component, set of components, or system that enables computing device 104 to detect articles of interest within a certain radius of the user geolocation, within a certain geographic location of the user, within the metes and bounds of a local, municipal, state, political, and/or geographical region. Articles of interest may be available to be acquired if they are available to be purchased and/or delivered to the user within the user geolocation. Computing device 104 may determine items are available to be purchased and/or delivered to the user within the user geolocation by receiving inputs using any network methodology as described herein. Information regarding availability of articles of interest that may be available to be acquired may be updated in real time. Computing device 104 selects an article of interest 108 after identifying articles of interest available to be acquired within the user geolocation. For example, computing device 104 may receive a transmission from a remote device 112 indicating that a user resides in Tampa, Florida Computing device 104 may identify articles of interest available to be acquired within Tampa, Florida such as for example a locally made perfume native to the Tampa, Florida area. Computing device 104 may select the perfume as an article of interest 108.

With continued reference to FIG. 1, computing device 104 may locate an article of interest 108 based on user input. Computing device 104 may include a graphical user interface. Graphical user interface 144 may include without limitation a form or other graphical element having display fields, where one or more elements of information may be displayed. Graphical user interface 144 may include sliders or other use inputs that may permit a user to indicate relative and/or absolute importance of a particular article of interest 108. Computing device 104 may display on graphical user interface 144 a plurality of conditional complaint 148. A "conditional complaint," as used in this disclosure, is a description of any problem that use of an article of interest 108 is intended to correct. A conditional complaint 148 may include a description of a condition on the skin such dry skin or redness upon waking. A conditional complaint 148 may include a description of a particular nail polish or eye shadow shade that a ser may considering using. A conditional complaint 148 may include a description of an issue relating to one's hair such as fizziness experienced during blow-drying. A conditional complaint 148 may include a description of a seasonal issue such as oiliness experienced in the T zone or itchy skin on one's hands in the winter. Computing device 104 receives a user entry selecting at least a conditional complaint 148. In an embodiment, a user may select using a slide on graphical user interface 144 a particular conditional complaint 148. In an embodiment, a user may select several conditional complaints 148 that may pertain to the user. Computing device 104 displays on a graphical user interface 144 a plurality of articles of interest associated with a selected conditional complaint 148. For example, a selected conditional complaint 148 such as itchy skin on face may prompt graphical user interface 144 to display articles of interest intended to correct itchy skin on face, including a moisturizer, a hydrocortisone cream, and a cucumber cooling gel. Computing device 104 receives a user entry selecting an article of interest 108 from the plurality of articles of interest.

With continued reference to FIG. 1, computing device 104 is configured to generate using ingredient training data 152 an ingredient metabolic classifier. "Ingredient training data," as used in this disclosure, is training data that includes a plurality of biological extraction 128 and a plurality of correlated ingredient metabolic profiles 156. An "ingredient metabolic profile," as used in this disclosure, is a collection of indicators as to a user's ability to absorb, and metabolize one or more ingredients and/or articles of interest, and/or topically effect a user's skin. Indicators may include any marker of chemical absorption, distribution, metabolism, and/or elimination, including for example an indicator of liver function, kidney function, gut function, and the like. Indicators may include topical effects such as the ability of one or more ingredients and/or articles of interest to cause an allergy, sensitivity, effect on a skin's microbiome population and the like. An "ingredient," as used in this disclosure, includes any component of an article of interest 108. An ingredient may include an active ingredient that may be biologically active and/or affect the therapeutic action of the article of interest. An ingredient may include a non-active ingredient which may include a component of an article of interest that does not affect the therapeutic action of the article of interest. In an embodiment, a non-active ingredient may include an inert ingredient that may include for example, a binding material, dye, preservative, and/or flavoring agent. In an embodiment, an ingredient may be the same as the article of interest 108. For example, an article of interest 108 such as red nail polish may include several ingredients including nitrocellulose, chromium oxide, mica, and thixotropy. In yet another non-limiting example, an article of interest 108 such as a hydrating serum may include water, glycerin, hydrolyzed hazelnut protein, carrageenan, and punica granatum. In an embodiment, an ingredient metabolic profile 156 may indicate that a user has compromised hepatic function and as such an ingredient such as parabens will be toxic when used in a hair-styling product but not when applied in a small amount in nail polish. In yet another non-limiting example, an ingredient metabolic profile 156 may indicate that a user has super-functioning liver and kidney function, and as such an ingredient such as phthalates contained within any article of interest 108 including for example shampoo, conditioner, hair gel, and body lotion will be adequately metabolized by the user.

With continued reference to FIG. 1, computing device 104 generates an ingredient metabolic classifier 160. An "ingredient metabolic classifier," as used in this disclosure, is a machine-learning model that sorts inputs into categories or bins of data using a classification algorithm. Ingredient metabolic classifier 160 utilizes a user biological extraction 128 as an input and outputs an ingredient metabolic profile 156. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, ingredient metabolic classifier 160 may generate an ingredient metabolic profile 156 that contains a plurality of ingredients containing metabolic impact label 164. A "metabolic impact label," as used in this disclosure is any indication as to the safety of use of an ingredient. A metabolic impact label 164 may indicate if a user should never use an ingredient. For example, a user with heavy metal toxicity may receive a metabolic impact label 164 that indicates the user should never use an article of manufacture that contains parabens. A metabolic impact label 164 may indicate if a user can occasionally use an article of manufacture that contains a particular ingredient. For example, a metabolic impact label 164 may indicate that a user can use an ingredient such as benzene contained within certain articles of interest such as those applied to the nails and hair but the user should not use benzene contained within any product being applied to the face or skin. A metabolic impact label 164 may indicate the frequency with which a user may apply an ingredient, for example a metabolic impact label 164 may indicate that a user may apply a lotion containing coconut oil no more than once per day. In an embodiment, a metabolic impact label 164 may indicate that a user can frequently use an article of manufacture.

With continued reference to FIG. 1, computing device 104 is configured to identify at least an ingredient contained within an article of interest 108. Computing device 104 may identify at least an ingredient contained within an article of interest 108 by evaluating an article of interest 108 to determine a manufacturer. A "manufacturer," as used in this disclosure, is any producer of an article of manufacture, and/or an article of interest and/or ingredients thereof. For example, DOVE DEEP MOISTURE BODY WASH is manufactured by Unilever of London, United Kingdom. In yet another non-limiting example, a VENUS SMOOTH WOMEN'S RAZOR is manufactured by Gillette, of Boston, Massachusetts Computing device 104 may determine a current ingredient list contained within an article of interest 108 from a manufacturer. Computing device 104 may do this utilizing any network methodology as described herein. In an embodiment, computing device 104 may identify ingredients contained within an article of interest 108 such as for example, ONE LOVE ORGANICS VITAMIN B CLEANSING OIL as produced by One Love Organics of St. Simons, Georgia which includes ingredients that include sunflower seed oil, papaya seed oil, and pumpkin seed oil. In an embodiment, one or more ingredients may be stored in an ingredient database 168 located on computing device 104 as described in more detail below. Ingredient database 168 may be implemented, without limitation, as a relational database, a key-value retrieval datastore such as a NOSQL database, or any other form or structure for use as a datastore that a person skilled in the art would recognize as suitable upon review of the entirety of this disclosure.

With continued reference to FIG. 1, computing device 104 is configured to determine the tolerability of an article of interest 108. "Tolerability," as used in this disclosure, is an indication of the degree to which an article of interest 108 can be tolerated by a user. Tolerability may refer to a degree and/or frequency that an article of interest 108 can be tolerated by a user. Tolerability may indicate how compatible an article of interest 108 is with a user's body. For example, computing device 104 may determine that an article of interest 108 is best tolerated if used no more than three days each week. In yet another non-limiting example, computing device 104 may determine that an article of interest 108 is not tolerated but another article of interest 108 may be better suited. Computing device 104 determines the tolerability of an article of interest 108 using a metabolic profile and at least an ingredient contained within the article of interest 108. Computing device 104 may compare at least an ingredient contained within an article of interest 108 to a metabolic profile to determine the tolerability of the article of interest 108. For example, computing device 104 may determine that an article of interest 108 such as a body lotion will be tolerated by a user because each of the three ingredients are listed within a metabolic profile as being compatible for the user. In yet another non-limiting example, computing device 104 may determine that an article of interest 108 will not be tolerated by a user because the article of interest 108 contains an ingredient such as isopropyl alcohol, which the user is unable to tolerate. In yet another non-limiting example, computing device 104 may determine that an article of interest 108 such as a shampoo will be tolerated by the user if used no more than three times each week because the shampoo contains an ingredient such as sodium lauryl sulfate which the user's ingredient metabolic profile 156 indicates as being tolerated in controlled doses and not exceeding daily usage.

With continued reference to FIG. 1, computing device 104 may use one or more machine-learning algorithms to determine tolerability. Computing device 104 may generate a tolerability machine-learning model 172 to determine tolerability. A "tolerability machine-learning model," as used in this disclosure, is a machine-learning model that utilizes a metabolic profile as an input and outputs a plurality of articles of interest tolerability labels. An "article of interest tolerability label," as used in this disclosure, is an indicator as to the tolerability of a particular article of interest 108. An article of interest tolerability label may include textual data. Tolerability includes any of the measures of tolerability as described above. For example, an article of interest 108 tolerability label may indicate that an article of interest 108 such as BIG APPLE RED OIL NAIL LACQUER as produced by OPI Products of North Hollywood, California is not tolerated by a user because it contains red dyes which the user is unable to metabolize, but NUDE OIL NAIL LACQUER as produced by OPI Products of North Hollywood, California is tolerated by the user because it does not contain red dyes. Computing device 104 generates a tolerability machine-learning model 172 which may include performing a series of one or more calculations, algorithms, and/or equations. Computing device 104 outputs a plurality of articles of interest tolerability labels 176 utilizing the tolerability machine-learning model 172. Computing device 104 determines the tolerability of the article of interest 108 using the plurality of output articles of interest tolerability labels. Computing device 104 may utilize output articles of interest tolerability labels 176 to suggest other articles of interest that may be better tolerated and/or better suited for a user.

With continued reference to FIG. 1, computing device 104 may make alternative recommendations and/or suggestions for an article of interest 108 when an article of interest 108 is not tolerated by a user. Computing device 104 may determine that an article of interest 108 is not tolerable for a user. This may be performed utilizing any of the methodologies as described above. Computing device 104 may identify a class category of an article of interest 108 that is not tolerable for a user. A "class category," as used in this disclosure, is a collection of one or more articles of interest that have shared characteristics. Shared characteristics may include similar purposes, similar uses, similar functions, similar characteristics and the like. For example, a class category may include nail polish, hair styling products, shaving products, makeup, products intended for women, products intended for men, parfum, cologne, anti-perspirants, deodorants, skin care products, soaps, and the like. Computing device 104 may identify a class category such as by consulting ingredient database 168. In an embodiment, articles of interest may be listed within ingredient database 168 by class category. Computing device 104 may locate an article of interest 108 contained within a class category that is tolerable for a user. Computing device 104 may locate an article of interest 108 contained within a class category by consulting ingredient database 168. Computing device 104 may select an article of interest 108 that is tolerable for a user by utilizing an article of interest 108 tolerability label. For example, computing device 104 may determine that an article of interest 108 such as an apricot face wash is not tolerable for a user based on an article of interest 108 tolerability label. In such an instance, computing device 104 may identify the apricot face wash as belonging to a class category of being a face wash, and as such locate an article of interest 108 such as a mango face wash that is tolerable for a user based on an article of interest 108 tolerability label. Computing device 104 may suggest the mango face wash instead, such as by transmitting the suggestion of the mango face wash to a remote device 112 and/or by displaying the mango face wash on a graphical user interface 144 for the user.

Figure 2:
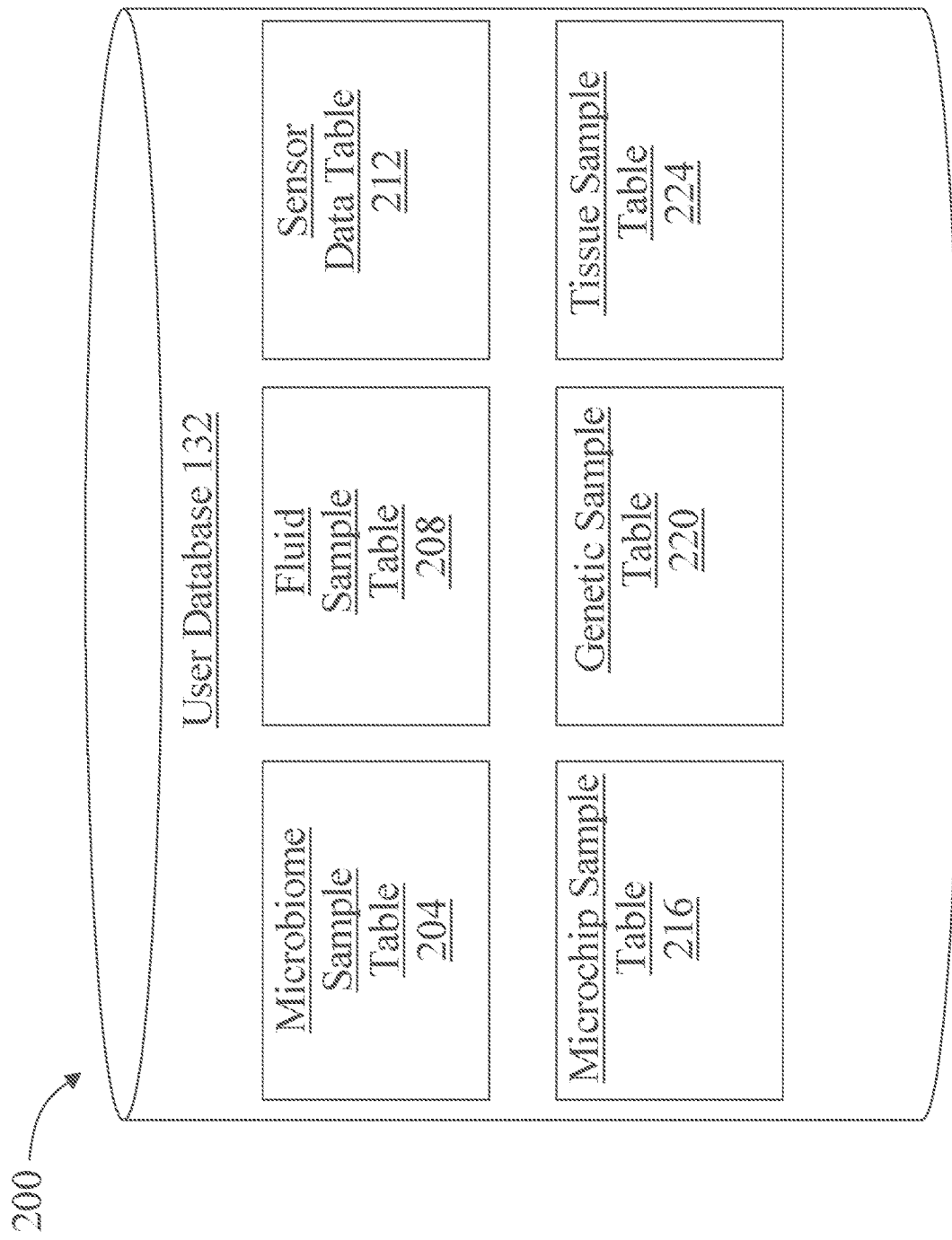
FIG. 2 is a block diagram illustrating an exemplary embodiment of a user database.

Referring now to FIG. 2, an exemplary embodiment of user database 132 is illustrated. User database 132 may be implemented as any data structure as described above in more detail. One or more tables contained within user database 132 may include microbiome sample table 204; microbiome sample table 204 may include one or more biological extraction 128 relating to the microbiome. For instance and without limitation, microbiome sample table 204 may include a physically extracted sample such as a stool sample analyzed for the presence of pathogenic species such as parasites and anaerobes. One or more tables contained within user database 132 may include fluid sample table 208; fluid sample table 208 may include one or more biological extraction 128 containing fluid samples. For instance and without limitation, fluid sample table 208 may include a urine sample analyzed for the presence or absence of glucose. One or more tables contained within user database 132 may include sensor data table 212; sensor data table 212 may include one or more biological extraction 128 containing sensor measurements. For instance and without limitation, sensor data table 212 may include heart rate, blood pressure, and glucose readings. One or more tables contained within user database 132 may include microchip sample table 216; microchip sample table 216 may include one or more biological extraction 128 obtained from a microchip. For instance and without limitation, microchip sample table 216 may include an intracellular nutrient level obtained from a microchip embedded under a user's skin. One or more tables contained within user database 132 may include genetic sample table 220; genetic sample table 220 may include one or more biological extraction 128 containing genetic samples. For instance and without limitation, genetic sample table 220 may include a blood test analyzed for the apolipoprotein E4 variant (APOE4). One or more tables contained within user database 132 may include tissue sample table 224; tissue sample table 224 may include one or more biological extraction 128 containing tissue samples. For instance and without limitation, tissue sample table 224 may include a bone marrow biopsy used to diagnosis leukemia.

Figure 3A:
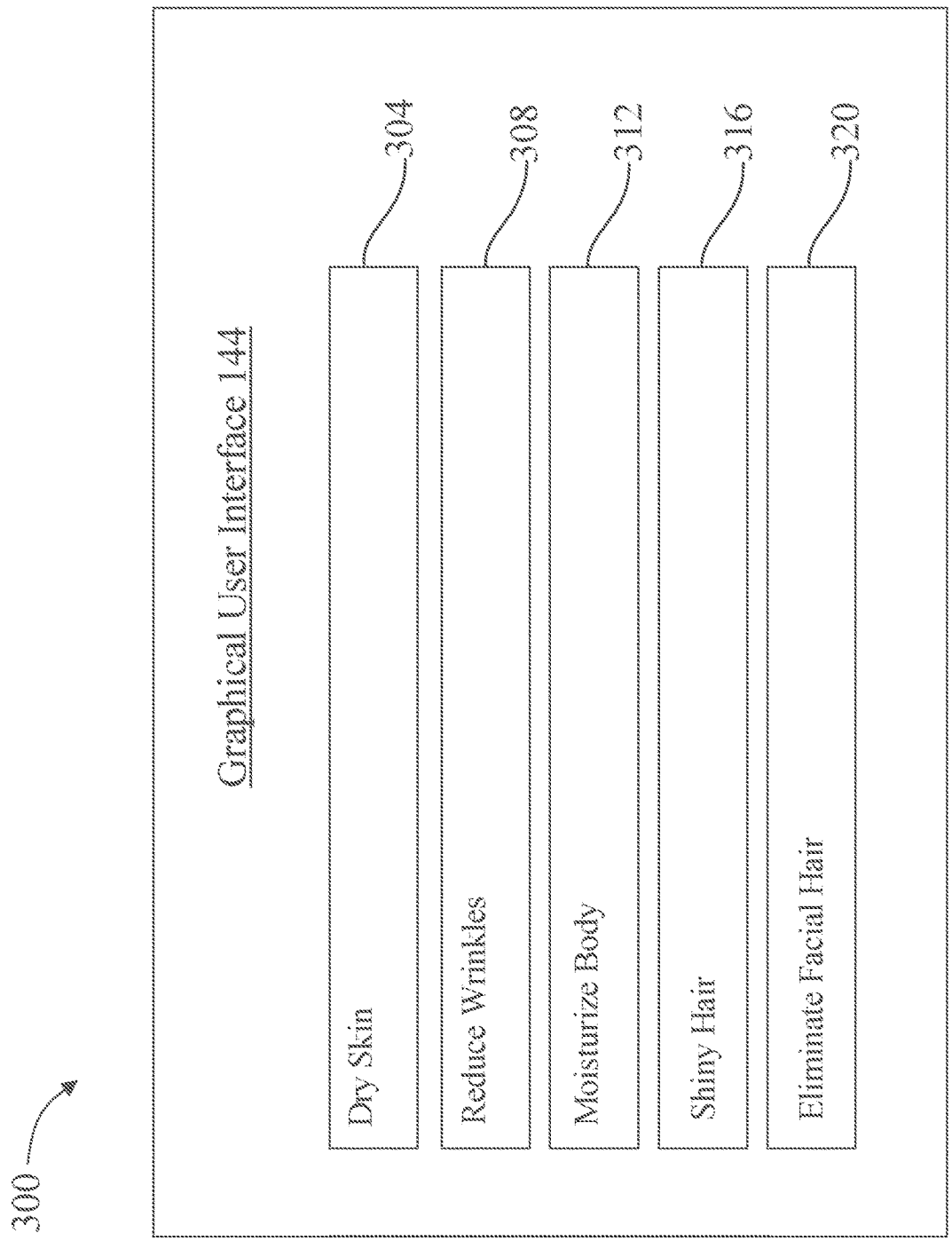
FIGS. 3A-3B are a diagrammatic representation of a graphical user interface.
Figure 3B:
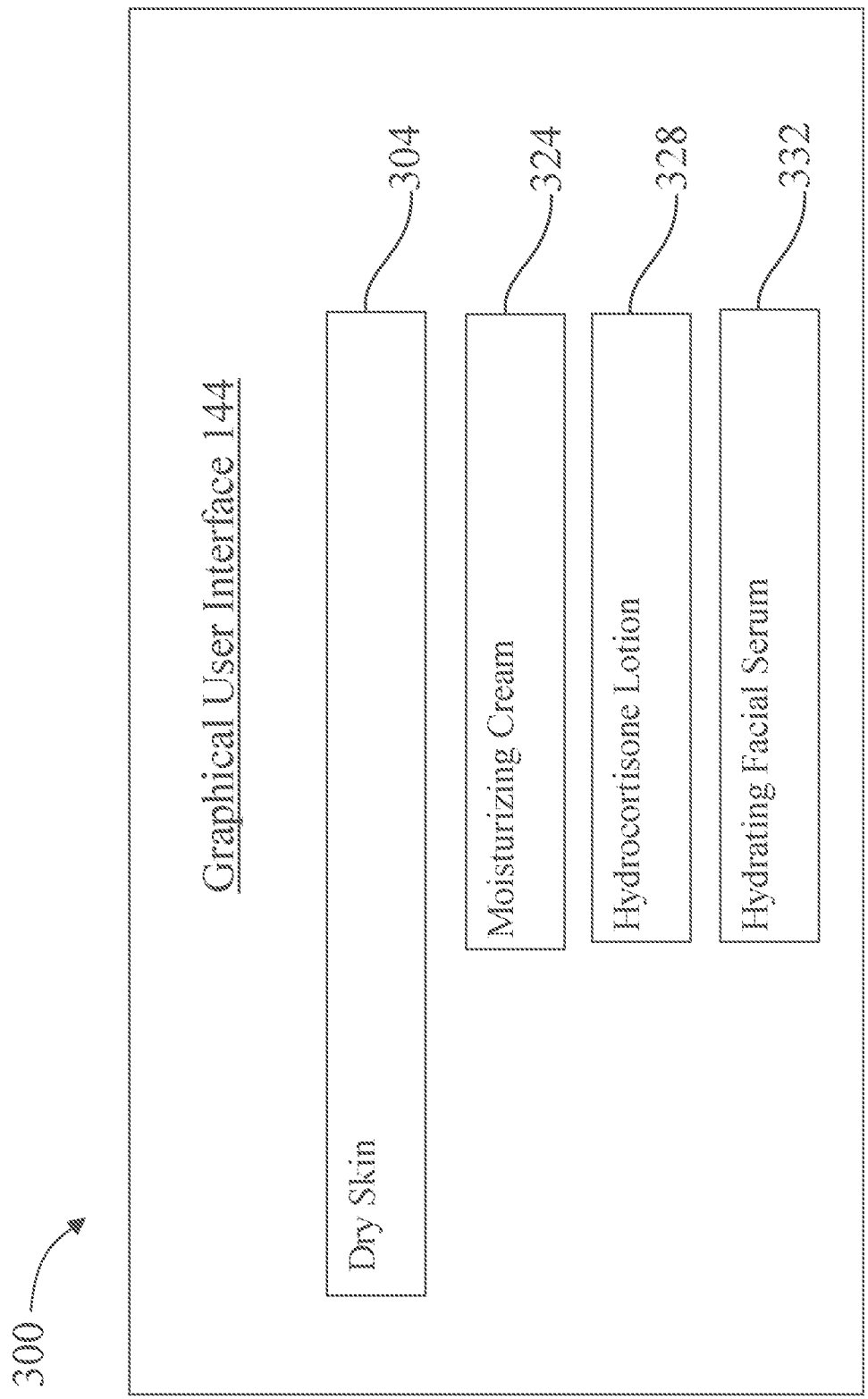

Referring now to FIGS. 3A-3B, an exemplary embodiment of graphical user interface 144 is illustrated. Referring to FIG. 3A, in an embodiment, graphical user interface 144 may display a plurality of conditional complaint 148. Conditional complaint 148 include any of the conditional complaint 148 as described above. Conditional complaint 148 may include for example but are not limited to dry skin 304, reduce wrinkles 308, moisturize body 312, shiny hair 316, and/or eliminate facial hair 320. A user may select one or more conditional complaint 148 displayed on graphical user interface 144 as described above in more detail. Referring now to FIG. 3B, upon selection of a conditional complaint 148, graphical user interface 144 may display a plurality of articles of interest associated with a selected conditional complaint 148. In an embodiment, a user may select a conditional complaint 148 such as dry skin 304, whereby graphical user interface 144 may display a plurality of articles of interest associated with dry skin 304 which could include for example moisturizing cream 324, hydrocortisone lotion 328, and/or hydrating facial serum 332. In an embodiment, computing device 104 may receive a user entry selecting an article of interest 108 from a plurality of articles of interest. For example, a user may select hydrating facial serum 332, which computing device 104 may utilize to determine the tolerability of.

Figure 4:
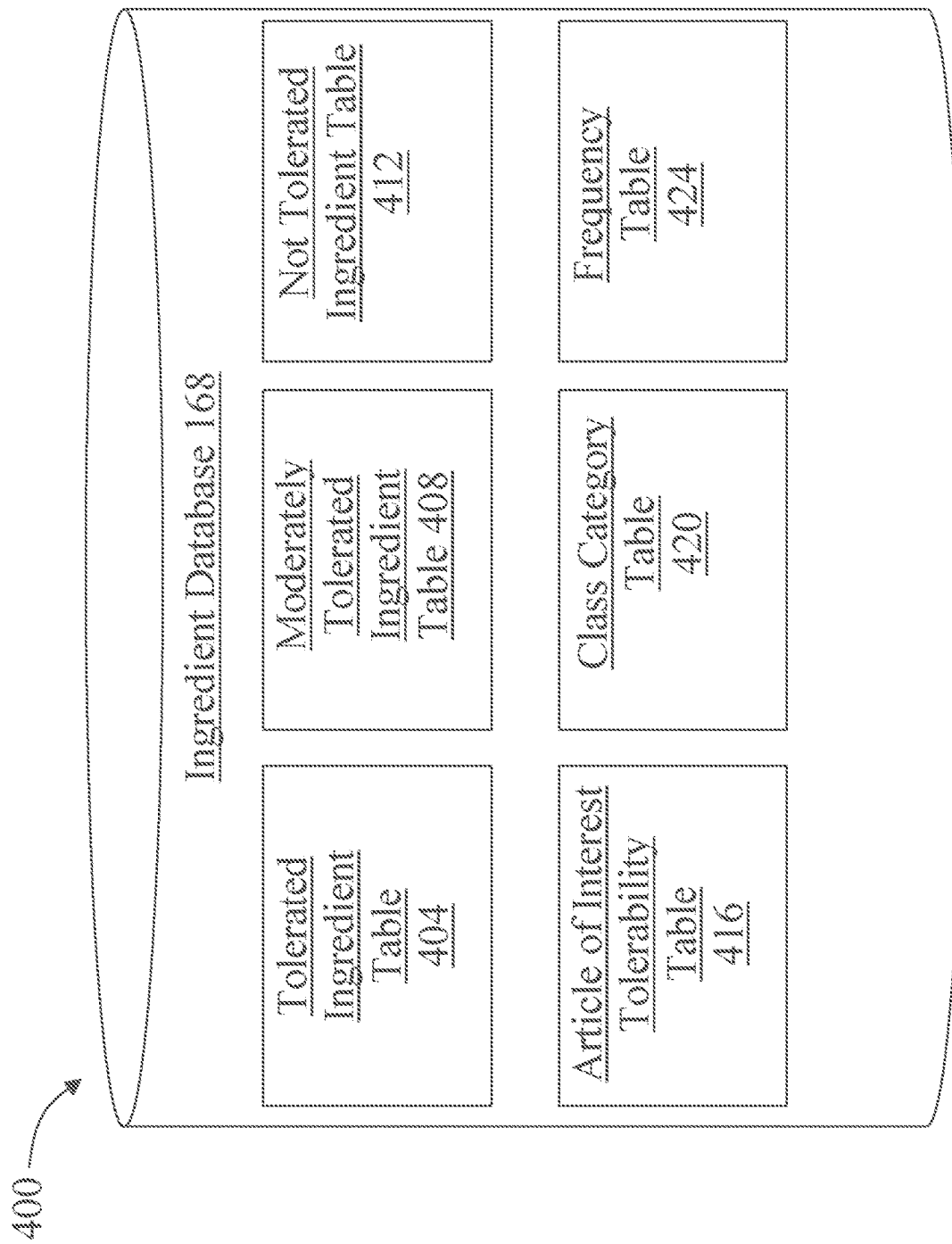
FIG. 4 is a block diagram illustrating an exemplary embodiment of an ingredient database.

Referring now to FIG. 4, an exemplary embodiment of ingredient database 168 is illustrated. Ingredient database 168 may be implemented as any data structure as described above. One or more tables contained within ingredient database 168 may include tolerated ingredient table 404; tolerated ingredient table 404 may include one or more ingredients tolerated by a user. For instance and without limitation, tolerated ingredient table 404 may include tolerated ingredients that include talc, alpha hydroxy acid, fragrance, squalene, and acacia catechu gum that are all tolerated by a user. One or more tables contained within ingredient database 168 may include moderately tolerated ingredient table 408; moderately tolerated ingredient table 408 may include one or more ingredients moderately tolerated by a user. For instance and without limitation, moderately tolerated ingredient table 408 may include moderately tolerated ingredients that include achillea millefolium extract, allantoin, gluconic acid, and squalene. One or more tables contained within ingredient database 168 may include not tolerated ingredient table 412; not tolerated ingredient table 412 may include one or more ingredients not tolerated by a user. For instance and without limitation, not tolerated ingredient table 412 may include not tolerated ingredients that include saccharin, kaolin, and tartaric acid. One or more tables contained within ingredient database may include article of interest 108 tolerability table 416; article of interest 108 tolerability table 416 may include one or more articles of interest each containing an article of interest 108 tolerability label. For instance and without limitation, article of interest 108 tolerability table 416 may include a first article of interest 108 such as vanilla body lotion that contains an article of interest 108 tolerability label that indicates it is not tolerated, and a second article of interest 108 such as lavender parfum that contains an article of interest 108 tolerability label that indicates it is tolerated. One or more tables contained within ingredient database 168 may include class category table 420; class category table 420 may include articles of interest containing class category indicators. For instance and without limitation, class category table 420 may include an article of interest 108 such as a red lipstick that contains a class category indicator of makeup and an article of interest 108 such as shampoo that contains a class category indicator of hair products. One or more tables contained within ingredient database 168 may include frequency table 424; frequency table 424 may include information describing how frequently an ingredient and/or article of interest 108 may be tolerated by a user. For instance and without limitation, frequency table 424 may contain information describing an ingredient such as parabens that can never be tolerated by a user but an article of interest 108 such as hair spray may be tolerated as frequently as a user feels is necessary.

Figure 5:
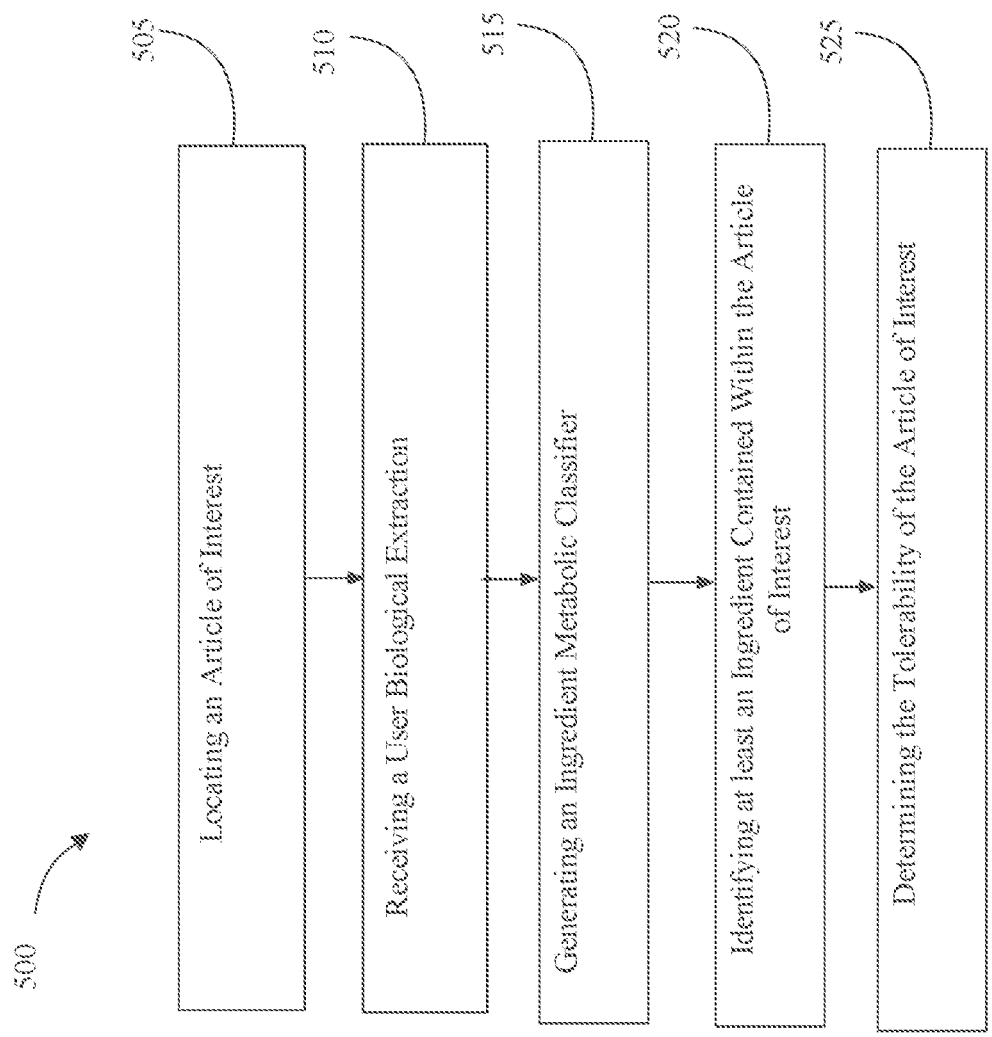
FIG. 5 is a process flow diagram illustrating an exemplary embodiment of a method of informing product decisions.

Referring now to FIG. 5, an exemplary embodiment of a method 500 of informing product decisions is illustrated. At step 505, a computing device 104 locates an article of interest 108 for a user. An article of interest 108 includes any of the articles of interest as described above in reference to FIGS. 1-4. An article of interest 108 includes any product intended to enhance and/or alter the appearance, fragrance, and/or texture of a human body. An article of interest 108 may include for example, a particular brand name shampoo such as AVEENO FRESH GREENS BLEND as produced by Johnson and Johnson of New Brunswick, New Jersey. In yet another non-limiting example, an article of interest 108 may include a category of articles of interest such as nail polish or hair products and the like. An article of interest 108 may be self-reported, such as if a user identifies an article of interest 108 and enters information regarding the article of interest 108 into a graphical user interface 144 located on computing device 104. In an embodiment, a user may transmit an article of interest 108 to computing device 104 from remote device 112. This may be performed utilizing any network methodology as described herein.

With continued reference to FIG. 5, computing device 104 may identify an article of interest 108 by generating a climate model. Computing device 104 may receive an element of user climate data 116 from a remote device 112. An element of user climate data 116 includes any of the elements of user climate data as described above in reference to FIGS. 1-4. For example, a user may generate an element of user climate data 116 that describes the climate where the user resides as being dry and cold in the winter and warm and wet in the summer and spring. Computing device 104 generates a climate machine-learning model 124. Climate machine-learning model includes any of the climate machine-learning models as described above in reference to FIGS. 1-4. In an embodiment, climate machine-learning model 124 may include a supervised machine-learning model, an unsupervised machine-learning model and/or a lazy-learning model. Climate machine-learning model 124 utilizes climate data as an input and outputs articles of interest. Computing device 104 identifies an article of interest 108 as a function of generating a climate machine-learning model 124.

With continued reference to FIG. 5, computing device 104 may locate an article of internet utilizing a user biological extraction 128. Computing device 104 generates using a clustering algorithm a biological model 140. Biological model 140 includes any of the biological model 140 as described above in reference to FIGS. 1-4. Biological model 140 is generated using biological training data 136. Biological training data 136 includes a plurality of biological extraction 128 and a plurality of correlated articles of interest. Computing device 104 generates biological model 140 using biological training data 136 and a clustering algorithm. Clustering algorithm includes any of the clustering algorithms as described above in reference to FIGS. 1-4. Clustering algorithms may include for example k-means clustering algorithm, centroid-based clustering algorithm, density based clustering algorithm, distribution based clustering algorithm, hierarchical clustering algorithm, and the like. Computing device 104 determines an article of interest 108 by generating biological model 140. Generating biological model 140 may include performing a series of one or more calculations, algorithms, and/or equations. Biological model 140 utilizes a biological extraction 128 as an input and outputs articles of interest.

With continued reference to FIG. 5, computing device 104 may locate an article of interest 108 using an element of user geolocation data 120. Computing device 104 may receive an element of user geolocation data 120 such as for example, entered onto graphical user interface 144 and/or received from a remote device 112. An element of user geolocation data 120 includes any of the elements of user geolocation data as described above in reference to FIGS. 1-4. For example, an element of user geolocation data 120 may include a global positioning system (GPS) location of a user. Computing device 104 identifies articles of interest available to be acquired within the user geolocation. Articles of interest available to be acquired include any articles of interest available for purchase, sale, and/or ability to be shipped to the user geolocation. Computing device 104 may identify articles of interest available to be acquired within the user geolocation by receiving inputs utilizing any network methodology as described herein. Computing device 104 selects an article of interest 108.

With continued reference to FIG. 5, computing device 104 locates an article of interest 108 based on one or more user inputs received on graphical user interface 144 located on computing device 104. Computing device 104 displays on a graphical user interface 144 a plurality of conditional complaint 148. Conditional complaint 148 include any of the conditional complaint 148 as described above in reference to FIGS. 1-4. For example, a conditional complaint 148 may include pale skin, dry nails, color enhancing lipstick, colored cheeks, and the like. Computing device 104 receives a user entry selecting at least a conditional complaint 148. In an embodiment, a user may use sliders contained within graphical user interface 144 to select one or more conditional complaint 148 that apply to the user. Computing device 104 displays on graphical user interface 144 a plurality of articles of interest associated with at least a selected conditional complaint 148. For example, a conditional complaint 148 such as makeup may prompt computing device 104 to display a plurality of articles of interest associated with makeup such as concealer, bronzer, blush, eyeshadow, mascara, lipstick, and eyeliner. In yet another non-limiting example, a conditional complaint 148 such as odor may prompt computing device 104 to display a plurality of articles of interest associated with odor such as perfume, cologne, eau de perfume, eau de toilette, and eau fraiche. Computing device 104 receives a user entry selecting an article of interest 108 from a plurality of articles of interest.

With continued reference to FIG. 5, at step 510, a computing device 104 receives a user biological extraction 128. A user biological extraction 128 includes any of the biological extraction 128 as described above in reference to FIGS. 1-4. For example, a user biological extraction 128 may include blood glucose readings obtained from a microchip embedded under a user's skin. In yet another non-limiting example, a user biological extraction 128 may include a blood sample analyzed for intracellular and extracellular nutrient levels. In an embodiment, a user biological extraction 128 may include a saliva sample analyzed for one or more hormone levels including estradiol, estrone, estriol, progesterone, testosterone, and cortisol.

With continued reference to FIG. 5, at step 515 a computing device 104 generates using ingredient training data 152 an ingredient metabolic classifier 160. Ingredient training data 152 includes any of the ingredient training data 152 as described above in reference to FIGS. 1-4. Ingredient training data 152 includes a plurality of biological extraction 128 and a plurality of correlated ingredient metabolic profile 156. Computing device generates ingredient metabolic classifier 160 using any of the classification algorithms as described above in reference to FIGS. 1-4. In an embodiment, computing device 104 may generate a naïve bayes classification algorithm. Ingredient metabolic classifier 160 inputs a user biological extraction 128 and outputs an ingredient metabolic profile 156. Ingredient metabolic profile 156 includes any of the ingredient metabolic profile 156 as described above in reference to FIGS. 1-4. Ingredient metabolic profile 156 includes a collection of indicators as to a user's ability to absorb and metabolize one or more ingredients and/or articles of interest. For example, ingredient metabolic profile 156 may indicate that a user is a super-absorber of parabens and as such cannot tolerate articles of interest that contain parabens as it will accumulate rapidly and cause toxicity in the user. In yet another non-limiting example, ingredient metabolic profile 156 may indicate that a user is a rapid metabolizer of sodium lauryl sulfate, and as such a user can tolerate any article of interest 108 that contains sodium lauryl sulfate. In an embodiment, an ingredient metabolic profile 156 may contain a plurality of ingredients containing metabolic impact label 164. Metabolic impact label 164 include any of the metabolic impact label 164 as described above in reference to FIGS. 1-4. Metabolic impact label 164 includes any indication as to the safety of use of an ingredient. For example, ingredient metabolic profile 156 may indicate that a user has adequate metabolism of glycerin, and as such, glycerin may contain a metabolic impact label 164 that indicates glycerin is safe for the user to utilize in any article of interest 108. In yet another non-limiting example, ingredient metabolic profile 156 may indicate that a user has impaired metabolism of sorbitol, and as such, sorbitol may contain a metabolic impact label 164 that indicates sorbitol is safe for use in articles of interest that are applied to the extremities including the hair, toenails, and fingernails, but not to the face.

With continued reference to FIG. 5, at step 520 computing device 104 identifies at least an ingredient contained within an article of interest 108. An ingredient includes any of the ingredients as described above in reference to FIGS. 1-4. Computing device 104 may identify an ingredient contained within an article of interest 108 by evaluating an article of interest 108 to determine a manufacturer. In an embodiment, a manufacturer of an article of interest 108 may be stored in ingredient database 168. Computing device 104 determines a current ingredient list contained within an article of interest 108 from a manufacturer. A "current ingredient list," as used in this disclosure, is a data entry containing a list of one or more ingredients contained within an article of interest. In an embodiment, a current ingredient list may be obtained from one or more manufactures for a single article of interest, such as when a first manufacturer produces a first ingredient contained within an article of interest and a second manufacturer produces a second ingredient contained within the same article of interest. In an embodiment, a current ingredient list contained within an article of interest 108 may be stored in ingredient database 168 and updated in real time. In an embodiment, computing device 104 may be configured to receive one or more updated ingredient lists from a computing device operated by a manufacturer utilizing any network transmission as described herein.

With continued reference to FIG. 5, at step 525 computing device 104 determines the tolerability of an article of interest 108. Tolerability includes any of the indicators of tolerance as described above in reference to FIGS. 1-4. Computing device 104 may determine tolerability of an article of interest by generating a tolerability machine-learning model 172. Tolerability machine-learning model 172 includes any of the tolerability machine-learning model 172 as described above in reference to FIGS. 1-4. Tolerability machine-learning model utilizes a metabolic profile as an input and outputs a plurality of articles of interest tolerability labels. Articles of interest tolerability labels 176 include any of the articles of interest tolerability labels 176 as described above in reference to FIGS. 1-4. Articles of interest tolerability labels 176 indicate the tolerability of a particular article of interest 108. Computing device 104 outputs a plurality of articles of interest tolerability labels 176 by generating tolerability machine-learning model 172. Generating tolerability machine-learning model 172 may include performing a series of one or more calculations, algorithms, and/or equations. Computing device 104 determines the tolerability of an articles of interest using the output plurality of articles of interest tolerability labels. For example, computing device 104 may match an article of interest 108 to an article of interest 108 tolerability label containing the article of interest 108 to determine what the tolerability indicates relating to the article of interest 108. In an embodiment, an article of interest 108 tolerability label may indicate that an article of interest 108 may be freely used and/or consumed by a user. In an embodiment, an article of interest 108 tolerability label may indicate that an article of interest 108 can be utilized with restrictions such as only at certain times of the day, only at a certain number of times each week, and/or only at certain areas and/or locations on the body.

With continued reference to FIG. 5, computing device 104 may determine that an article of interest 108 is not compatible for a user, such as when an article of interest 108 tolerability label indicates that an article of interest 108 should never or very infrequently be utilized by a user. Computing device 104 identifies a class category of an article of interest 108. A class category includes any of the class categories as described above in reference to FIGS. 1-4. In an embodiment, a class category may be stored within ingredient database 168. Computing device 104 locates an article of interest 108 contained within the class category that is tolerable for a user. Computing device 104 may locate an article of interest 108 within a class category that is tolerable for a user utilizing articles of interest tolerability labels. Computing device 104 may locate articles of interest that contain tolerability labels that indicate tolerability and locate such articles of interest that are contained within a class category that is deemed to be tolerable for a user.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
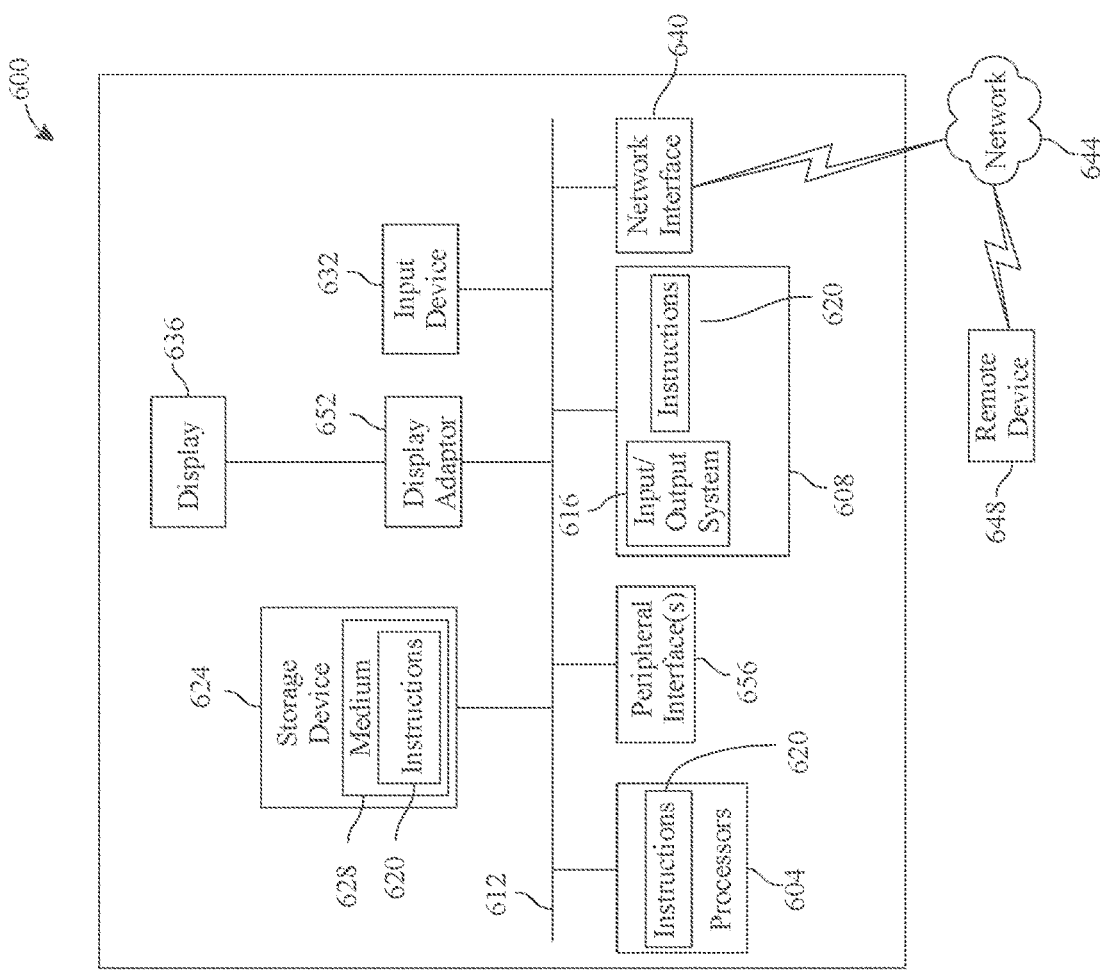
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for informing product decisions, the system comprising a computing device, the computing device designed and configured to:
   receive a conditional complaint relating to a user;
   retrieve at least one biological extraction relating to the user, wherein a plurality of biological extractions are inputted into a biological model, wherein the biological model is generated using a classification algorithm, and wherein the biological model further outputs one or more articles of interest intended to correct the conditional complaint;
   select an article of interest intended to correct the conditional complaint;
   generate, a classifier, wherein the classifier comprises a machine-learning model trained by training data including the plurality of biological extractions and the plurality of correlated articles of interest, and wherein the classifier is configured to receive the user biological extraction as an input and output a tolerability score as a function of the training data; and
   display the tolerability score.

2. The system of claim 1, wherein the conditional complaint identifies a dermatological concern.

3. The system of claim 1, wherein the conditional complaint is identified as a function of the biological extraction relating to the user.

4. The system of claim 3 further comprising:
   generating a machine-learning model wherein the machine-learning model utilizes the biological extraction relating to the user and the conditional complaint as inputs to the machine-learning model and outputs from the machine-learning model the article of interest; and
   selecting the article of interest as a function of the machine-learning model.

5. The system of claim 1, wherein the conditional complaint is identified as a function of an element of user climate data.

6. The system of claim 1, wherein selecting the article of interest further comprises:
   generating a query within an ingredient database for the conditional complaint;
   locating a plurality of articles of interest related to the conditional complaint; and
   selecting the article of interest from the plurality of articles of interest as a function of an element of user geolocation data.

7. The system of claim 1, wherein selecting the article of interest further comprises:
   receiving an input from the user identifying a manufacturer; and
   selecting the article of interest as a function of the manufacturer.

8. The system of claim 1, wherein selecting the article of interest further comprises:
   identifying a metabolic impact label as a function of the biological extraction; and
   selecting the article of interest as a function of the metabolic impact label.

9. The system of claim 1, wherein the tolerability score further comprises instructions for how to use the article of interest.

10. The system of claim 1, wherein the tolerability score further comprises displaying a second article of interest to be used in conjunction with the article of interest.

11. A method of informing product decisions, the method comprising:
    receiving by a computing device, a conditional complaint relating to a user;
    retrieving by the computing device, at least one biological extraction relating to the user, wherein a plurality of biological extractions are inputted into a biological model, wherein the biological model is generated using a classification algorithm, and wherein the biological model further outputs one or more articles of interest intended to correct the conditional complaint;
    selecting by the computing device, an article of interest intended to correct the conditional complaint;
    generating by the computing device, a classifier, wherein the classifier comprises a machine-learning model trained by training data including the plurality of biological extractions and the plurality of correlated articles of interest, and wherein the classifier is configured to receive the user biological extraction as an input and output a tolerability score as a function of the training data; and displaying by the computing device, the tolerability score.

12. The method of claim 11, wherein the conditional complaint identifies a dermatological concern.

13. The method of claim 11, wherein the conditional complaint is identified as a function of the biological extraction relating to the user.

14. The method of claim 13 further comprising:

generating a machine-learning model wherein the machine-learning model utilizes the biological extraction relating to the user and the conditional complaint as inputs to the machine-learning model and outputs from the machine-learning model the article of interest; and selecting the article of interest as a function of the machine-learning model.

15. The method of claim 11, wherein the conditional complaint is identified as a function of an element of user climate data.

16. The method of claim 11, wherein selecting the article of interest further comprises:

generating a query within an ingredient database for the conditional complaint;

locating a plurality of articles of interest related to the conditional complaint; and selecting the article of interest from the plurality of articles of interest as a function of an element of user geolocation data.

17. The method of claim 11, wherein selecting the article of interest further comprises:

receiving an input from the user identifying a manufacturer; and selecting the article of interest as a function of the manufacturer.

18. The method of claim 11, wherein selecting the article of interest further comprises:

identifying a metabolic impact label as a function of the biological extraction; and selecting the article of interest as a function of the metabolic impact label.

19. The method of claim 11, wherein the tolerability score further comprises instructions for how to use the article of interest.

20. The method of claim 11, wherein the tolerability score further comprises displaying a second article of interest to be used in conjunction with the article of interest.

* * * * *